United States Patent [19]

Cohen et al.

[11] Patent Number: 5,066,783

[45] Date of Patent: * Nov. 19, 1991

[54] ANTIVIRAL PEPTIDES AND MEANS FOR TREATING HERPES INFECTIONS

[76] Inventors: Eric A. Cohen, 2175 Stevens, St. Laurent, Quebec, Canada, H4M 1G6; Pierrette Gaudreau, 776 Andrien, Greenfield Park, Quebec, Canada, J4V 3L4; Jacques Michaud, 115 Ste. Catherine, O. Apt. #302, Montreal, Quebec, Canada, H2V 4R3; Paul Brazeau, 12460 Odette Oligny, Cartierville, Montreal, Quebec, Canada, H4J 9Z7; Yves Langelier, 4671 Christophe Colomb, Montreal, Quebec, Canada, H2J 3G7

[*] Notice: The portion of the term of this patent subsequent to Jan. 3, 2006 has been disclaimed.

[21] Appl. No.: 244,879

[22] Filed: Sep. 15, 1988

Related U.S. Application Data

[63] Continuation-in-part of Ser. No. 46,707, May 7, 1987, Pat. No. 4,795,740.

[51] Int. Cl.$^5$ ............................................. C07K 7/06
[52] U.S. Cl. .................................... 530/328; 530/329; 530/330
[58] Field of Search ........................ 530/328, 329, 330

[56] References Cited

U.S. PATENT DOCUMENTS

| | | | |
|---|---|---|---|
| 4,795,740 | 1/1989 | Cohen et al. | 514/14 |
| 4,814,432 | 3/1989 | Freidinger et al. | 530/329 |
| 4,837,304 | 6/1989 | Garsky et al. | 530/328 |
| 4,845,195 | 7/1989 | Colonno et al. | 530/330 |

FOREIGN PATENT DOCUMENTS

| | | |
|---|---|---|
| 81303266.1 | 7/1981 | European Pat. Off. . |
| 86105507.7 | 4/1986 | European Pat. Off. . |
| 3100974 | 1/1982 | Fed. Rep. of Germany . |
| 175566 | 6/1978 | Netherlands . |
| 179055 | 9/1978 | Netherlands . |
| 181036 | 12/1978 | Netherlands . |
| 7938574 | 11/1979 | United Kingdom . |
| 2062643 | 5/1981 | United Kingdom ...................... 530/ |

OTHER PUBLICATIONS

B. M. Dutia, H. S. Marsden et al., *Nature* 321, 439–441 (1986).
*Chemical Abstracts*, 103, 215768.
Kitada et al., *Pept. Chem.* 22: 43-8 (1985) Chemical Abstract 103, 215768n.

*Primary Examiner*—Mary C. Lee
*Assistant Examiner*—Michael G. Ambrose
*Attorney, Agent, or Firm*—Foley & Lardner

[57] ABSTRACT

Disclosed herein are antiviral peptides of the formula $A\text{-}R^8\text{-}R^9\text{-}R^{10}\text{-}R^{11}\text{-}R^{12}\text{-}R^{13}\text{-}R^{14}\text{-}R^{15}B$ wherein A is from zero up to seven amino acid residues and includes a terminal hydrogen or a terminal N-acyl, or A is a phenylpropionyl with optional substitution of the para position of the phenyl, $R^8$, $R^9$, $R^{10}$, $R^{13}$, $R^{14}$ and $R^{15}$ are various amino acid residues with the stipulation that one or more of the three amino acid residues immediately preceeding $R^{11}$ and $R^{12}$ are independently Val, D-Val, Nva, D-Nva, Leu, D-Leu, Nle, D-Nle, Ile or D-Ile, and B is hydroxy, amino or lower alkylamino. The antiviral activity of the peptides can be enhanced by combining them with a protease inhibitor. The peptides and the combination are useful for the treatment of herpes viral infections in mammals.

1 Claim, 2 Drawing Sheets

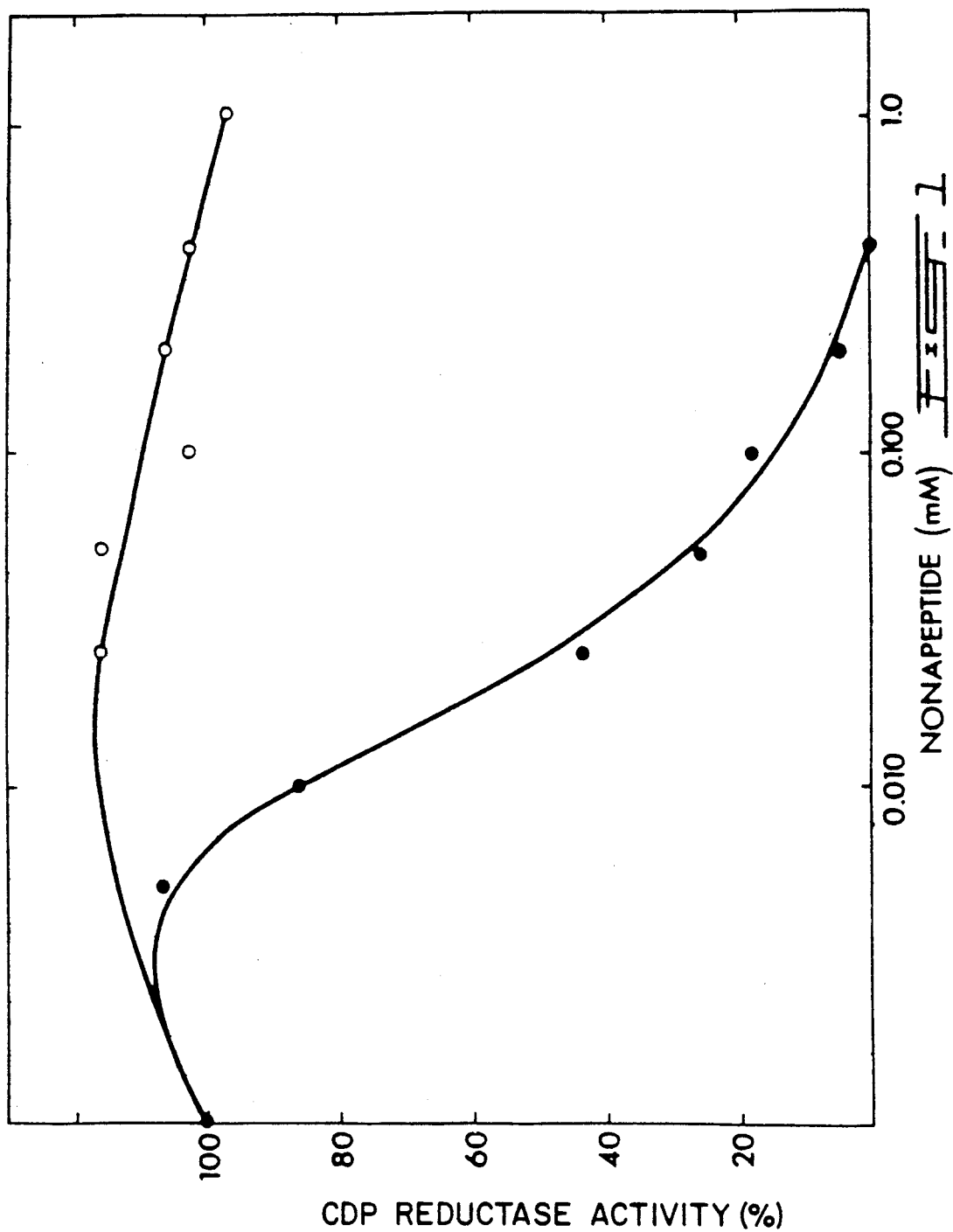

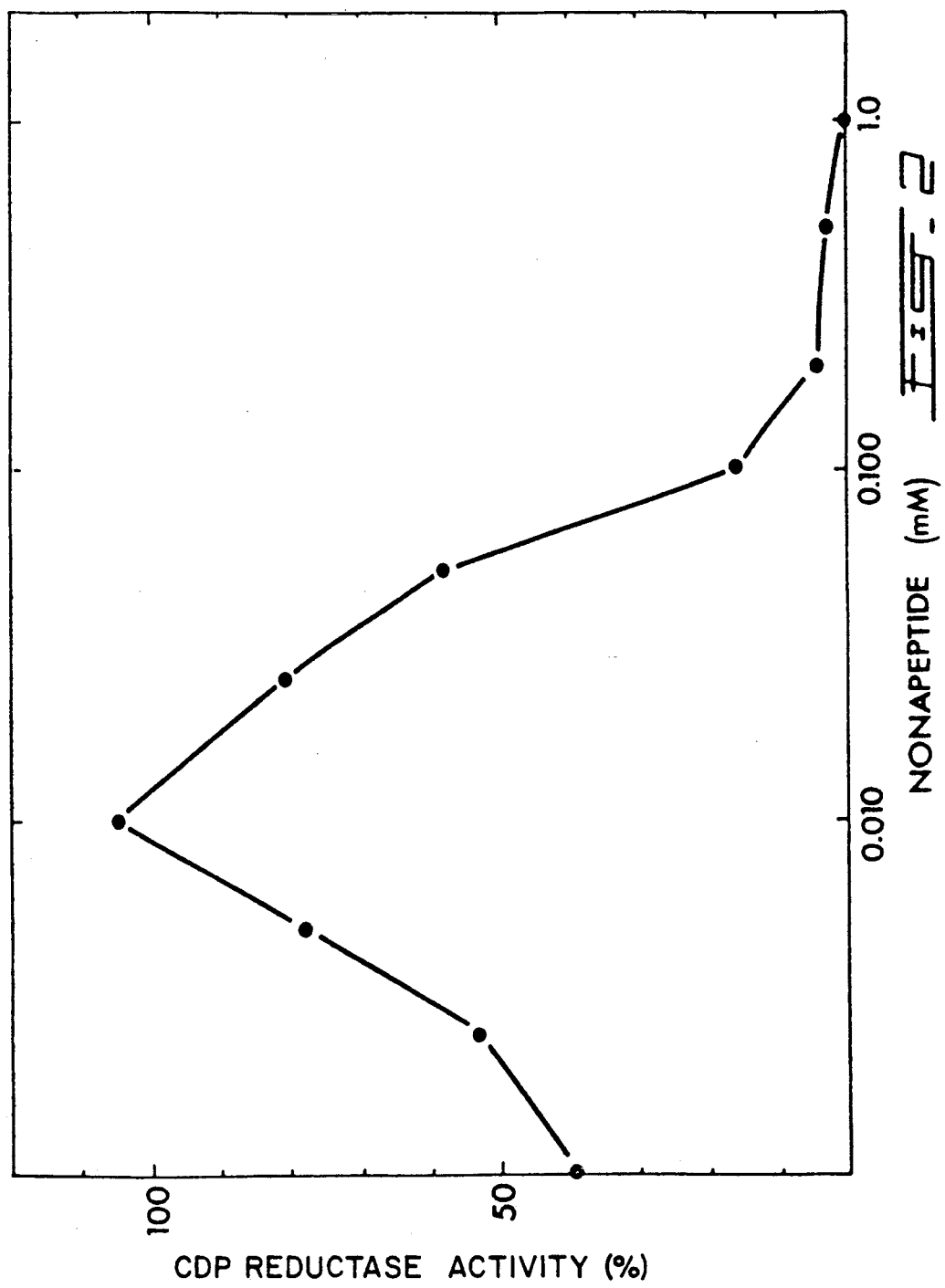

ANTIVIRAL PEPTIDES AND MEANS FOR TREATING HERPES INFECTIONS

CROSS REFERENCE TO RELATED APPLICATIONS

This application is a continuation-in-part of application Ser. No. 07/046,707, filed May 7, 1987, now U.S. Pat. No. 4,795,740.

FIELD OF THE INVENTION

The present invention relates to peptides having antiviral activity and to means for using the peptides to treat viral infections. More specifically, this invention relates to oligopeptides having antiviral properties, to processes for their production, to pharmaceutical compositions comprising the peptides, to pharmaceutical compositions comprising a combination of one of the peptides with a protease inhibitor, to methods for treating viral infections, and to antibodies of the peptides which are useful as reagents for the detection of the virus by immunoassay techniques.

BACKGROUND OF THE INVENTION

The need for effective antiviral agents continues to exist, especially antiviral agents with an improved therapeutic ratio.

Unexpectedly, we have found that a group of peptides exhibit antiviral properties against herpes viruses with apparently no deleterious effects on the host subject.

The association of peptides with antiviral activity is unusual, but has been reported before. The subject peptides of the previous reports are distinguished from the present peptides by differences in their chemical structure and in their spectrum of activity. Instances of previous reports include: H. Umezawa et al., Canadian Patent 1,098,850, issued Apr. 7, 1981; P.W Choppin et al., J. Infect. Dis., 143, 352 (1981); and P. W. Choppin et al., in "Targets for the Design of Antiviral Agents", E. Declercq and R. T. Walker, eds., Plenum Press, New York, 1984, pp 287–305.

A noteworthy property of the peptides of this application is the enhancement of their antiviral activity when they are combined with a protease inhibitor, for example, the antibiotic bacitracin. In this context, it is interesting to note that bacitracin, when used alone, has been reported as being inactive against HSV-1 by A. Alarcon et al., Antiviral Research, 4, 231 (1984); and that bacitracin in combination with neomycin and glycyrrhizin has been proposed for treating oral infections, R. Segal et al., U.K. Patent Application 2167296, published May 29, 1986. Hence, the enhancement of the antiviral activity realized with the straight forward combination of the peptides and a protease inhibitor represents an unexpected turn of events.

SUMMARY OF THE INVENTION

The antiviral peptides of this invention are represented by formula 1

$A-R^8-R^9-R^{10}-R^{11}-R^{12}-R^{13}-R^{14}-R^{15}-B$  b 1 wherein A is L-(aa)$_{0-6}$-R$^7$- wherein L is hydrogen or lower acyl; aa is an amino acid residue derived from an amino acid selected the group of

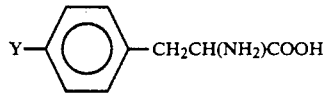

(wherein Y is lower alkyl, lower alkoxy, amino, nitro, azido or halo), norleucine, norvaline, B-alanine, the natural amino acids excluding cystine, and any of the enantiomorphic forms thereof (each of the aa in the radical aa $_{2-6}$ being the same or a different amino acid residue in relation to aa$_1$), and R$^7$ is an amino acid residue derived from an amino acid selected from the group of

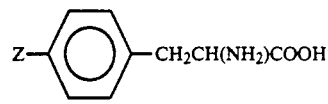

(wherein Z is hydrogen, lower alkyl, lower alkoxy, amino, nitro, azido, halo or hydroxy), His and Trp, and any of the enantiomorphic forms thereof; or A is

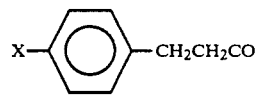

wherein X is hydrogen, lower alkyl, lower alkoxy, amino, nitro, azido, halo or hydroxy; and R$^8$, R$^9$, R$^{10}$, R$^{13}$, R$^{14}$ and R$^{15}$ are independently an amino acid residue (aa) as defined hereinabove; R$^{11}$ and R$^{12}$ are independently Val, D-Val, Nva, D-Nva, Leu, D-Leu, Nle, D-Nle, Ile or D-Ile; and B is hydroxy, amino or lower alkyl amino; or a therapeutically acceptable salt thereof; provided that when A is L-(aa)$_0$-R$^7$ wherein L, aa and R$^7$ are as defined herein then one or more of R$^7$, R$^8$, R$^9$, and R$^{10}$ may be deleted as long as that when the deletion is only one of R$^8$, R$^9$ or R$^{10}$ then R$^7$, R$^{11}$, R$^{12}$, R$^{13}$, R$^{14}$ and R$^{15}$ are not Tyr, Val, Val, Asn, Asp, Leu, respectively, and the remaining two amino acid residues of R$^8$, R$^9$ and R$^{10}$ are not Gly and Ala, respectively.

A preferred group of the peptides of this invention is represented by formula 1 wherein A is L-(aa)$_{0-6}$-R$^7$- wherein L is hydrogen or lower acyl; aa is an amino acid residue derived amino acid selected from the group of

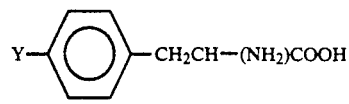

(wherein Y is halo), norleucine, norvaline, the natural amino acids excluding cystine, and any of the enantiomorphic forms thereof (each of the aa in the radical aa$_{2-6}$ being the same or a different amino acid residue in relation to aa$_1$), and R$^7$ is an amino acid residue derived from an amino acid selected from the group of

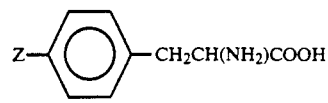

(wherein Z is hydrogen, halo or hydroxy), His and Trp, and any of the enantiomorphic forms thereof; or A is

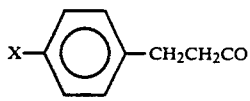

wherein X is hydrogen, halo or hydroxy, and $R^8$, $R^9$, $R^{10}$, $R^{13}$, $R^{14}$ and $R^{15}$ are independently an amino acid residue (aa) as defined in this paragraph; $R^{11}$ and $R^{12}$ are independently Val, D-Val, Nva, or D-Nva; and B is hydroxy, amino or lower alkyl amino; or a therapeutically acceptable salt thereof.

Another preferred group of the peptides of this invention is represented by formula 1a $$L-R^1-R^2-R^3-R^4-R^5-R^6-R^7$$
$$-R^9-R^{10}-R^{11}-R^{12}-R^{13}-R^{14}-R^{15}-B \qquad 1a$$

wherein L is hydrogen or lower acyl; $R^1$ to $R^6$, inclusive, $R^9$, $R^{10}$ and $R^{13}$ to $R^{15}$, inclusive, are independently an amino acid re (aa) as defined hereinabove; $R^7$ is

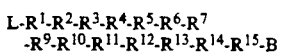

wherein Z is hydrogen, lower alkyl, alkoxy, amino, nitro, azido, halo or hydroxy, or any of the enantiomorphic forms thereof; $R^8$ is Ala, D-Ala, Thr, D-Thr, Leu, 0-Leu, Ile or D-Ile; $R^{11}$ and $R^{12}$ are independently Val, D-Val, Nva, D-Nva, Leu, D-Leu, Nle, D- Nle, Ile or D-Ile; and B is hydroxy or amino; provided that any or all of the residues $R^1$ to $R^6$, inclusive, may be deleted; or a therapeutically acceptable salt thereof.

Still another preferred group of the peptides of this invention is represented by formula 1b

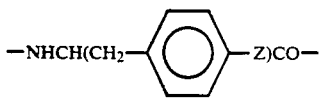

wherein X is hydrogen, lower alkyl, lower alkoxy, amino, nitro, azido, halo or hydroxy, and $R^8$, $R^9$, $R^{10}$, $R^{11}$, $R^{12}$, $R^{13}$, $R^{14}$ and $R^{15}$ are as defined hereinabove for formula 1; and B is hydroxy or amino; or a therapeutically acceptable salt thereof.

A more preferred group of the peptides is represented by formula 1a in which L is hydrogen or acetyl, $R^1$ is Glu, Val or des-$R^1$, $R^2$ is Cys, Leu, Ile, Ser, Gln or des-$R^2$,$R^3$ is Arg, Gln or des-$R^3$, $R^4$is Ser or des-$R^4$, $R^5$ is Thr, Ser or des-$R^5$, $R^6$is Ser, Asp, 4-NH -Phe, 4-NO$_2$-Phe or des-$R^6$, $R^7$ is Tyr, Tyr(Me) or D-Tyr, $R^8$ is Ala, β-Ala or Thr, $R^9$is Gly or Met, $R^{10}$ is Ala, Thr or Leu, $R^{11}$ is Val, Nva, Leu, Nle or Ile, $R^{12}$ is Val, Nva, Leu, Nle or Ile, $R^{13}$is Asn or Asp, $R^{14}$is Asp, $R^{15}$is Leu, and B is hydroxy or amino; or a therapeutically acceptable salt thereof.

Another more preferred group of the peptides is represented by formula 1 wherein A is H-Tyr, Ac-Tyr, H-D-Trp, Ac-D-Trp, H-Tyr(Me), Ac-Tyr(Me), H-Phe, Ac-Phe, desamino-Tyr, H-(4-NH$_2$-Phe)-Tyr or H-(4-NO$_2$-Phe)- Try; $R^8$ is Ala, D-Ala, B-Ala, Cys, Ser, Sar, Thr or des-$R^8$; $R^9$ is Gly, Val, Pro, Met or des-$R^9$, $R^{10}$ is Ala, Leu, Val, Cys, Phe, Thr, Ser or des-$R^{10}$, $R^{11}$ and $R^{12}$ are independently Val, Ile or Leu, $R^{13}$ is Asn, Asp or Gln, $R^{14}$is Asp, $R^{15}$is Leu or Ile and B is hydroxy or amino, or a therapeutically acceptable salt thereof; provided that when A is H-Tyr and $R^8$ is des-$R^8$ then $R^9$, $R^{10}$, $R^{11}$, $R^{12}$, $R^{13}$, $R^{14}$ and $R^{15}$ are not Gly, Ala, Val, Val, Asn, Asp and Leu, respectively.

A most preferred group of the peptides is represented by formula 1 wherein the radical A-$R^8$-$R^9$-$R^{10}$ is selected from the group consisting of H-Tyr-Ala-Gly-Ala, Ac-Tyr-Ala-Gly-Ala, H-Tyr(Me), Ac-Tyr(Me), H-Tyr-Ala-Gly-Thr, Ac-Tyr-Ala-Gly-Thr, desamino-Tyr-Ala-Gly-Ala, desamino-Tyr-Ala-Gly-Thr, H-Tyr, Ac-Tyr, H-Phe, Ac-Phe and desamino-Tyr, $R^{11}$ and $R^{12}$ are independently Val or Ile, $R^{13}$ is Asn, Asp or Gln, $R^{14}$is Asp, $R^{15}$is Leu and B is hydroxy, or a therapeutically acceptable salt thereof.

Another most preferred group of peptides is represented by formula when the radical A-$R^8$-$R^9$-$R^{10}$ is selected from the group consisting of H-Tyr-Ala-Gly-Thr, Ac-Tyr-Ala-Gly-Thr, desamino-Tyr-Ala-Gly-Thr, Ac-Tyr-Ala-Gly-Phe, Ac-Tyr(OAc)-Ala-Gly-Phe, Ac-Tyr-Ala-Gly-Ser, Ac-Tyr-Ala-Gly-Val, Ac-Tyr-Ala-Gly-Cys, Ac-Tyr-Ala-Ala-Thr, Ac-Tyr-Ala-Val-Thr, Ac-Tyr-Ser-Gly-Thr and Ac-Tyr-Cys-Gly-Thr, the radical $R^{11}$-$R^{12}$ is selected from the group consisting of Val-Val, Val-Ile and Ile-Val, the radical $R^{13}$-$R^{14}$-$R^{15}$ is selected from the group consisting of Asn-Asp-Leu and Asp-Asp-Leu, and B is hydroxy, or a therapeutically acceptable salt thereof.

One aspect of this invention involves a pharmaceutical composition comprising an anti-herpes virally effective amount of a compound of formula 1, or a therapeutically acceptable salt thereof, and a pharmaceutically or veterinarily acceptable carrier.

Another aspect of this invention involves a pharmaceutical composition comprising an anti-herpes virally effective amount of a combination of a protease inhibitor and a compound of formula 1, formula 1a or formula 1b, or a therapeutically acceptable salt thereof, and a pharmaceutically or veterinarily acceptable carrier.

Another aspect of this invention involves a method of treating herpes viral infection in a mammal by administering to the mammal an anti-herpes virally effective amount of the peptide of formula 1, formula 1a or formula 1b, or a therapeutically acceptable salt thereof, as defined hereinabove.

Another aspect of this invention involves a method of treating herpes viral infection in a mammal by administering to the mammal an anti-herpes virally effective amount of a combination of a protease inhibitor and a peptide of formula 1, formula 1a or formula 1b, or a therapeutically acceptable salt thereof, as defined hereinabove.

Still another aspect of the invention relates to antibodies to certain peptides of formula 1. The antibodies can be used as reagents for the detection of the virus in competitive immunoassays or immunometric assays.

Processes for preparing the peptides of formula 1 are described hereinafter.

BRIEF DESCRIPTION OF THE DRAWINGS

FIG. 1 shows the discriminating effects of increasing concentrations of H-Tyr-Ala-Gly-Ala-Val-Val-Asn-Asp-Leu-OH, a peptide of this invention, on ribonucleotide reductases purified from herpes simplex virus type 1 (strain F) - infected confluent BHK-21/C13 cells and exponentially growing 96-V-2(600) cells; ribonucleotide reductase being an essential enzyme for the synthesis of deoxyribonucleotides which are required by the virus and by the cell for replication.

FIG. 2 shows the specific effect of the peptide noted for FIG. 1 on the viral ribonucleotide reductase - neutralizing activity of an antiserum against the peptide.

DETAILS OF THE INVENTION

In general, the abbreviations used herein for designating the amino acids and the protective groups are based on recommendations of the IUPAC-IUB Commission on Biochemical Nomenclature, see Biochemistry, 11, 1726–1732 (1972). For instance, Ser, Tyr, D-Trp, Sar, D-Nle, Nva, Leu, Ile, Arg, Ala, β-Ala, Tyr(Me) and Gly represent the 'residues' of L-serine, L-tyrosine, D-trytophan, L-sarcosine, D-norleucine, L-norvaline, L-leucine, L-isoleucine, L-arginine, L-alanine, L-β-alanine, L-$O^4$-methyltyrosine and glycine, respectively. The term 'residue', when used with reference to an amino acid, means a radical derived from the corresponding amino acid by eliminating the hydroxyl of the carboxyl group and one hydrogen of the amino group. The symbol "4-NH$_2$-Phe" represents the residue 4-amino-L-phenylalanyl, i.e. (s)-α-amino-(4-aminobenzene)propanoyl. Similarly, 4-NO$_2$-Phe represents the residue of 4-nitro-L-phenylalanyl.

The term 'natural amino acid' means an amino acid which occurs in nature or which is incorporated as an amino acid residue in a naturally occurring peptide, exclusive of the amino acid cystine. Such amino acids are described, for example, in general textbooks of peptide chemistry; for example, K. D. Kopple, "Peptides and Amino Acids", W. A. Benjamin, Inc., New York, 1966, and E. Schröder and K. L. Lübke, "The Peptides", Vol. 1, Academic Press, New York, 1965, and include alanine, arginine, asparagine, aspartic acid, cysteine, glutamic acid, glutamine, glycine, histidine, hydroxylysine, hydroxyproline, isoleucine, leucine, lysine, methionine, phenylalanine, proline, pyroglutamic acid, sarcosine, serine, threonine, tryptophane, tyrosine and valine.

The term 'halo' as used herein means a halo radical selected from bromo, chloro, fluoro or iodo.

The term 'lower alkyl' as used herein means straight chain alkyl radicals containing one to four carbon atoms and branched chain alkyl radicals containing three or four carbon atoms and includes methyl, ethyl, propyl, butyl, 1-methylethyl, 2-methylpropyl and 1,1-dimethylethyl.

The term 'lower alkoxy' as used herein means straight chain alkoxy radicals containing one to four carbon atoms and branched chain alkoxy radicals containing three or four carbon atoms and includes methoxy, ethoxy, 1-methylethoxy, propoxy and butoxy.

The term 'pharmaceutically acceptable carrier' or 'veterinarily acceptable carrier' as used herein means a non-toxic, generally inert vehicle for the active ingredient which does not adversely affect the ingredient.

The term 'lower acyl' means an alkanoyl group containing two of four carbon atoms and includes acetyl, 1-oxopropyl etc, or an alkanoyl group containing three to ten carbon atoms wherein one of the carbon atoms is substituted with an amino group and includes for example 8-amino-1-oxooctanyl.

The term 'physiologically acceptable carrier' as used herein means an acceptable cosmetic vehicle of one or more non-toxic excipients, which do not react with the active ingredients contained therein or reduce their effectiveness.

The term 'protease inhibitor' means an agent capable of inhibiting the hydrolysis or proteolysis of peptides by proteases. Suitable protease inhibitors are the commercially available amastatin, antipain, epiamastatin, aprotinin, chymostatin, leupeptin, and preferably bacitracin or its therapeutically acceptable salts. Bacitracin and its therapeutically acceptable salts, for instance, zinc bacitracin, manganese bacitracin, sodium bacitracin and bacitracin methylenedisalicylic acid, are described by G. A. Brewer in 'Analytical Profiles of Drug Substances', volume 9, Academic Press, New York, N.Y. USA, 1980, pp 1–69.

The term 'effective amount' means a predetermined antiviral amount of the antiviral agent, i.e. an amount of the agent sufficient to be effective against the viral organisms in vivo.

The peptides of formula 1 are prepared by a suitable method such as by exclusively solid-phase techniques, by partial solid-phase techniques and/or by fragment condensation, or by classical solution couplings. For example, the techniques of exclusively solid-phase synthesis are described by J. M. Stewart and J. D. Young in the textbook 'Solid-Phase Peptide Synthesis', W. H. Freeman & Co., San Francisco, 1969, pp. 40–49. The fragment condensation method is exemplified by the disclosure of Canadian Patent 1,178,950, issued Dec. 4, 1984. Other available synthesis are exemplified by U.S. Pat. No. 3,842,067, issued Oct. 15, 1974, and U.S. Pat. No. 3,862,925, issued Jan. 28, 1975.

Common to such syntheses is the protection of the labile side chain groups of the various amino acid residues with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the o-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Thus, the aforementioned intermediate compounds are included within the scope of the invention.

Still another method for preparing the peptides within the scope of the invention employs recently developed recombinant DNA techniques. Recombinant DNA techniques suitable for the preparation of the peptides of this invention having amino acid residues of the natural amino acids are well known. For example, see L. Villa-Komaroff et al., Proc. Natl. Acad. Sci. USA, 75. 3727(1978).

The terminal amino acylated derivatives of the peptides of formula 1 are obtained from the corresponding free terminal amino peptides by treatment with a suitable acylating agent; for instance, the appropriate acid chloride or acid anhydride in the presence of a strong organic base, e.g. triethylamine.

The disclosures of the aforementioned publications by Stewart and Young and by Villa-Komaroff et al., and Canadian Patent 1,178,950, U.S Pat. Nos. 3,842,067 and 3,862,925 are herein incorporated by reference.

In an embodiment of the exclusively solid-phase technique, compounds of formula 1a in which $R^{15}$ is Leu are prepared as follows: α-amino protected leucine, preferably t-butyloxycarbonylleucine, is coupled to a chloromethylated resin with the aid of cesium bicarbonate. Following the coupling of the α-amino protected leucine to the resin support, the α-amino protecting group is removed, for example by using trifluoroacetic acid in methylene chloride or hydrochloric acid in dioxane. The deprotection is carried out at a temperature between about 0° C. and room temperature. Other standard cleaving reagents and conditions for removal of specific α-amino protecting groups may be used as described by E. Schröder and K. Lübke, supra, pp.72-75. After removal of the α-amino protecting group, the remaining α-amino (or β-amino) protected amino acids are coupled stepwise in the desired order to obtain the desired peptide. Each protected amino acid is introduced into the solid phase reactor in about a four-fold excess and the coupling is carried out in a medium of methylene chloride or mixtures of dimethylformamide in methylene chloride. In cases where incomplete coupling has occurred, the coupling procedure is repeated before removal of the amino protecting group, prior to the addition of the next amino acid to the solid phase reactor. The success of the coupling reaction at each stage of the synthesis is monitored by the ninhydrin reaction as described by E. Kaiser et al., Anal. Biochem., 34, 595(1970).

After the desired amino acid sequence has been synthesized, the protected peptide is removed from the resin support by treatment with hydrogen fluoride to give the corresponding free acid peptide. The peptide can also be separated from the resin by transesterification with a lower alkanol, preferably methanol or ethanol, in the presence of triethylamine. Thereafter, the recovered ester is purified by liquid chromatography. The collected fraction may be subjected to treatment with ammonia or a (lower alkyl)amine to convert the lower alkyl ester, preferably the methyl or ethyl ester, to the carboxyterminal amide or (lower alkyl)amide; note that the dinitrophenylsulfenyl or tosyl group, if present on a histidyl residue, will also be cleaved. The remaining side chain protecting groups of the protected peptide are then cleaved by procedures described above, for example by treatment with sodium in liquid ammonia or by hydrogen fluoride. Removal of the protected peptide from the resin support may also be carried out with ammonia to give the corresponding amide.

Alternatively, when it is desired to obtain the peptides as the amide (I,B=NH$_2$), the peptide can be prepared by the solid phase method using 1% cross-linked benzylhydrylamine (BHA) or p-methylbenzhydrylamine (MBHA) resin, incorporating the cleavage of the resin-coupled peptide and any required deprotection according to known procedures; for example, see G. R. Matsueda and J. M. Stewart, Peptides, 2, 45 (1981).

The peptides of formula 1 of this invention can be obtained in the form of therapeutically acceptable salts.

In the instance where a particular peptide has a residue which functions as a base, examples of such salts are those with organic acids, e.g. acetic, lactic, succinic, benzoic, salicyclic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxyl group, example of such salts are those with the sodium, potassium or calcium cations, or with strong organic bases, for example, triethylamine or N-ethylmopholine.

In general, the therapeutically acceptable salts of the peptides are biologically fully equivalent to the peptides themselves.

The antiviral activity of the peptides of formula 1 and the combination (i.e. the combination of the protease inhibitor and the peptides of formula 1a 1, or a therapeutically acceptable salt thereof) can be demonstrated by biochemical, microbiological and biological procedures showing the inhibitory effect of the peptides on the replication of herpes simplex viruses, types 1 and 2 (HSV-1 and HSV-2); and other herpes viruses, for example, varicella zoster virus (VZV), Epstein Barr virus (EBV), equine herpes virus (EHV) and pseudorabies virus (PRV).

Noteworthy is the fact that all of the aforementioned viruses are dependent on their own ribonucleotide reductase to synthesize deoxyribonucleotides for their replication. Although this fact may not be directly linked with the antiviral activity of the peptides or the combination of this invention, the peptides or the combination have been shown so far to have antiviral properties against all viruses dependent on ribonucleotide reductase to synthesis DNA for their replication.

In the examples hereinafter, the inhibitory effect of some of the peptides are noted with respect to the specific inhibition of herpes ribonucleotide reductase.

Noteworthy, in the connection with the specific inhibition of herpes ribonucleotide reductase, is the absence of such an effect on cellular ribonucleotide reductase activity required for normal cell replication.

Another method for demonstrating the inhibitory effect of the peptides or the combination on viral replication is the herpes virus yield assay; see, for example, T. Spector et al., Proc. Natl. Acad. Sci. USA, 82, 4254(1985). This method in a modified form is exemplified hereinafter.

A method for demonstrating the therapeutic effect of the peptides and the combination is the guinea pig model for cutaneous herpes simplex viral infections; see, for example, S. Alenius and B. Oberg, Archives of Virology, 58, 277 (1978). A modification of this method is exemplified hereinafter.

When a peptide of this invention, or its therapeutically acceptable salts, is employed alone as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen rout of administration and standard biological practice. For example, the peptide of formula 1 can be employed topically. For topical application, the peptide may be formulated in the form of a solution, cream, or lotion in pharmaceutically acceptable vehicles containing 0.1-10 percent, preferably 2 to 5 percent of the agent, and may be administered topically to the infected area of the body, e.g. the skin, eye or part of the oral or genital cavity.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

When the peptide, or its therapeutically acceptable salt, is utilized in combination with the protease inhibitor for treating viral infections, the combination is administered topically to warm blooded animals, e.g. humans, pigs or horses, in a vehicle comprising one or more pharmaceutically acceptable carriers, the proportion of which is determined by the solubility and chemical nature of the protease inhibitor and peptide, chosen route of administration and standard biological practice. For example, the two active agents (i.e. the protease inhibitor and the peptide of formula 1 or a therapeutically acceptable salt thereof) can be formulated in the form of solutions, emulsions, creams, or lotions in pharmaceutically acceptable vehicles. Such formulation can contain 0.01-0.2 percent, preferably 0.05 to 0.2 percent, by weight of the peptide and about 0.5 to 3, preferably 0.8 to 1.5, molar equivalents of the protease inhibitor with respect to the peptide.

One preferred embodiment of the combination involves an antiviral pharmaceutical composition for treating herpes viral infections of the eye, mouth or skin. This composition comprises a combination of 0.01 to 0.2 percent by weight of bacitracin or zinc bacitracin (specific activity ranging from 40 to 65 units per mg) and 0.01 to 0.2 percent of the peptide of formula 1a or 1b, as defined hereinbefore, together with a pharmaceutically acceptable carrier. Preferred carriers in this instance are water soluble ointment bases or water-oil type emulsions.

Examples of suitable excipients or carriers for the above mentioned formulations are found in standard pharmaceutical texts, e.g. in "Remington's Pharmaceutical Sciences", 16th ed, Mack Publishing Company, Easton, Penna., 1980.

The dosage of the peptides or the combination will vary with the form of administration and the particular active agent or agents chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the peptide or the combination is most desirably administered at a concentration level that will generally afford antiviral effective results without causing any harmful or deleterious side effects.

With reference to topical application, the peptide of formula 1 or the combination is administered cutaneously in one of the aforementioned topical formulation to the infected area of the body, e.g. the skin or part of the oral or genital cavity, in an amount sufficient to cover the infected area. The treatment should be repeated, for example, every four to six hours until lesions heal, usually within 3 to 4 days. No contraindications have been observed. Although this method of treating herpes viral infections can be most advantageously practiced by administering the combination of the protease inhibitor and the peptide of formula 1 simultaneously in a formulation, the separate or sequential administration on a daily basis of the two active agents is also encompassed within the scope of this invention.

With reference to systemic administration, the peptide of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Although the formulations disclosed herein are effective and relatively safe medications for treating herpes viral infections, the possible concurrent administration of these formulations with other antiviral medications or agents to obtain beneficial results is not excluded. Such other antiviral medications or agents include acyclovir (see Example 4), and antiviral surface active agents or antiviral interferons such as those disclosed by S. S. Asculai and F. Rapp in U.S. Pat. No. 4,507,281, Mar. 26, 1985.

Another important property of the peptides of formula 1 is their capacity to raise antibodies, namely immunoglobulins G (IgG). For example, by following standard immunization methods, an antipeptide serum can be isolated from a mammal, for example, a rabbit or a goat, previously injected with a conjugate of the peptide and methylated bovine serum albumin. Subsequent purification of the antiserum yields the IgG. See Example 2 for details.

These IgG antibodies specifically recognize and immunologically react with herpes simplex ribonucleotide reductase, or its $H_1$ or $H_2$ subunits. The latter property of the antibodies renders them useful as new reagents for the detection and serologic determination of herpes virus according to established immunoassay techniques, preferably the double antibody solid phase technique, using radioactive, luminescent, fluorescent or enzyme markers. A description of the immunoassay techniques including those for competitive and two-site immunometric assays, appear in "Immunoassays for the 80's", A. Voller et al., eds, University Park Press, Baltimore, Md., U.S.A., 1981, and in "Molecular Immunology, A Textbook", M. Z. Atassi et al., eds, Marcel Dekker, Inc., New York and Basel, 1984, both textbooks herein incorporated by reference.

The following examples illustrate further this invention.

EXAMPLE 1

Preparation of
L-tyrosyl-L-alanyl-glycyl-L-alanyl-L-valyl-L-valyl-L-asparagyl-L-aspartyl-L-leucine
(H-Tyr-Ala-Gly-Ala-Val-Val-Asn-Asp-Leu-OH)

The title compound was synthesized by the solid-phase technique of B. Merrifield, J. Amer. Chem. Soc., 85, 2149 (1963) employing a commercially available chloromethylated resin (1% cross linked, Aldrich Chemical Co.). N-Boc-L-leucine was esterified to the resin by the cesium salt method, B. F. Gisin, Helv. Chim. Acta, 56, 1476 (1973), at a loading of 0.64 meq/g. Couplings were performed using symmetrical anhydrides, J. Hagenmaier and J. Frank, Hoppe-Seyler's Z. Physiol. Chem., 353, 1973 (1972), until completion as evaluated by ninhydrin tests, Kaiser et al., supra. N-Boc groups were removed with a solution of trifluoroacetic acid in methylene chloride (40% V/V). Cleavage of the peptide from the solid support and removal of the protecting group, namely the 0-benzyl ester and the 0-2,6-dichlorobenzyloxycarbonyl protecting groups, was accomplished with hydrogen fluoride containing 10% (V/V) of distilled anisole (30 min, −20° C.; 30 min, 0° C.). The crude peptide was purified, in one step, by reverse phase HPLC on a Magnum 20 ® preparation column (50×2.2. cm, Partisil-10 ®, ODS-3, Whatman ®), using a concave gradient of 0–10% (V/V) acetonitrile in 0.01 M ammonium acetate. Overall yield was 74%. The product i.e. the title compound, gave the expected amino acid analyses after acidic hydrolysis and leucine aminopeptidase digest.

By following the procedure of this example but using the appropriate protected amino acids to give the required sequence, the following peptides of formula 1 were obtained.

H-Glu-Cys-Arg-Ser-Thr-Ser-Tyr-Ala-Gly-Ala-Val-Val-Asn-Asp-Leu-OH, hereinafter designated HSV 1-15;

H-Ser-Thr-Ser-Tyr-Ala-Gly-Ala-Val-Val-Asn-Asp-Leu-OH, hereinafter designated HSV 4-15;

H-Tyr-Thr-Met-Leu-Val-Val-Asp-Asp-Leu-OH, hereinafter designated EBV 7-15; and

H-Val-Ser-Arg-Ser-Thr-Ser-Tyr-Ala-Gly-Ala-Val-Val-Asn-Asp-Leu-OH, hereinafter designated HSV 1-15*.

Examples of other peptides of formula 1 which can be prepared by the procedure of Example 1 are:

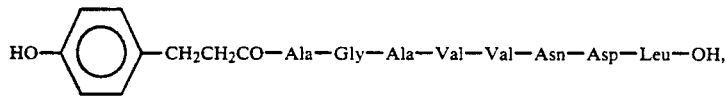

H-Ala-Gly-Ala-Val-Val-Asn-Asp-Leu-OH,
H-Ala-Val-Val-Asn-Asp-Leu-OH,

H—Tyr—Ala—Gly—Thr—Val—Ile—Asn—Asp—Leu—OH,

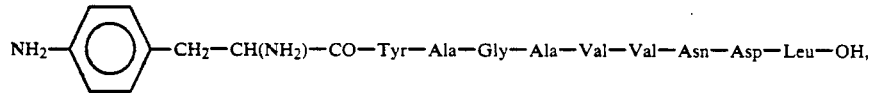

CH3CO-Ser-Thr-Ser-Tyr-Ala-Gly-Ala-Val-Val-Asn-Asp-Leu-OH,
H-Ser-Thr-D-Ser-Tyr-D-Ala-Gly-Ala-Val-Val-Asn-Asp-Leu-COOH,
H-Tyr-D-Thr-Gly-Ala-D-Val-D-Val-Leu-Ala-Leu-COHN2 H-Met-Ala-Asn-Ser-Ile-Asn-D-Trp-D-Ala-Gly-Ala-Nva-Nva-Asn-Leu-Ala-COOH, and H-Glu-Gln-Glu-Ser-Ser-Asp-Tyr-Thr-Met-Leu-Val-Val-Asp-Asp-Leu-OH.

EXAMPLE 2

Specific Inhibition of HSV-1 or HSV-2 Ribonucleotide Reductase by the Title Compound of Example 1

The viral and cellular ribonucleotide reductases were respectively partially purified from HSV-1 (strain F)-infected confluent BHK-21/C13 cells and exponentially growing 96-V-2(600) cells by precipitation of the cell extract with ammonium sulfate; see E. A. Cohen et al., J. Gen. Virol., 66, 733(1985). Aliquots of the viral (50 μg with a specific activity of 30 U mg$^{-1}$) or cellular (40 μg with a specific activity of 34 U mg$^{-1}$) enzyme preparation were mixed with increasing concentrations of the title compound of Example 1, hereafter referred to as the nonapeptide HSV 7-15. Ribonucleotide reductase activity was then assayed by monitoring the reduction of cytidine diphosphate (CDP) as described by Cohen et al., supra. The standard reaction mixture, in a final volume of 60 μl, contained: 50 mM, N-2-hydroxyethyl-piperazine-N$_1$-2-ethanesulfonic acid (pH 7.8); 4 mM, MgCl$_2$; 4 mM, ATP; 4 mM, NaF; 6 mM, DL-dithiothreitol (DTT); 54 μM, CDP; and 0.25 μCi, ($^3$H)-CDP. For the viral enzyme activity, MgCl$_2$ and ATP, which are nonessential for that activity, were usually omitted and 20 mM DTT was used. These changes did not affect the inhibition by the nonapeptide.

After 30 min. of incubation at 37° C. the reaction was stopped by immersing the tube in boiling water for 4 min. The precipitate was removed by centrifugation. Nucleotides in the supernatant were converted to nucleosides by enzymatic hydrolysis. The deoxyribonucleosides were subsequently separated from the ribonucleosides by ascending polyethyleneimine (PEI)-cellulose chromatography. One unit (U) of ribonucleotide reductase activity is defined as the amount of enzyme generating 1 nmol of dCDP/h under the standard assay conditions. The results, shown in FIG. 1, are expressed as a percentage of the activity obtained in the controls without nonapeptide HSV 7-15.

As shown in FIG. 1, fifty per cent inhibition was observed with 22 μM nonapeptide and total inhibition was obtained with a concentration of 400 μM. The curve obtained for the HSV-2 enzyme was nearly identical (data not shown). The cellular enzyme extracted from 96-V-2(600) (see FIG. 1) or BHK21/C13 cells (data not shown) was completely insensitive to the presence of the peptide in the assay up to 1 mM.

The following experiment was performed to demonstrate that the specific inhibitory effect of the nonapeptide HSV 7-15 was an inherent property of the peptide and not attributable to an artifact:

The anti-nonapeptide HSV 7-15 serum (P9) was obtained by rabbit immunization with the nonapeptide conjugated to methylated bovine serum albumin as described by R. Benoit et al., Proc. Natl. Acad. Sci. USA, 79, 917 (1982). IgG's were purified from the serum by adsorption to a column of protein A Sepharos ® CL-4B (Pharmac ®) followed by elution with 0.1 M glycine (pH 2.5). After the incubation of 5 μg of P9 IgG's with increasing concentrations of the nonapeptide for 30 min. at 20° C., 50 μg of partially purified HSV-1 ribonucleotide reductase (specific activity 30 U mg$^{-1}$) were added to each sample. Following a second incubation of 30 min. at 20° C., ribonucleotide reductase activity was assayed as described previously in this example.

Accordingly, 5pg of purified IgG (which gave 60% neutralization in absence of peptide) were preadsorbed with increasing concentrations of the nonapeptide and preincubated with 50 μg of viral enzyme before the ribonucleotide reductase assay. As can be seen in FIG. 2, at low nonapeptide concentrations, the capacity of the IgG to neutralize the enzyme activity was progressively eliminated until equivalence was reached at 10 μM. Subsequently, the activity was inhibited but the curve was displaced to the right relative to that in FIG. 1 as expected if the nonapeptide HSV 7-15 is responsible for the inhibition.

EXAMPLE 3

The specific inhibition of HSV ribonucleotide reductase activity of other peptides of this invention, for instance of peptides listed in Example 1, was demonstrated in the assay procedure of Example 2. Table I shows the specific inhibiting activity found for an illustrative group of these peptides in the assay.

TABLE 1

| | % CDP REDUCTASE ACTIVITY[a] | | | | |
|---|---|---|---|---|---|
| | HSV 7-15[b] | HSV 4-15[c] | HSV 1-15*[d] | HSV 1-15[e] | EBV 7-15[f] |
| 0 μM | 100 | 100 | 100 | 100 | 100 |
| 10 μM | 96 | 87 | 96 | 97 | 100 |
| 25 μM | 94 | 71 | 90 | 70 | 100 |
| 50 μM | 80 | 47 | 60 | 47 | 100 |
| 100 μM | 45 | 18 | 26 | 24 | 70 |
| 400 μM | 9 | 11 | 11 | 7 | 10 |

[a]Ammonium sulfate-purified HSV-1 (strain F)-infected cell protein extracts (75 μg) were assayed for CDP (cytidine diphosphate) reductase activity in presence of absence of the synthetic peptides.
[b]HSV 7-15 = H—Tyr—Ala—Gly—Ala—Val—Val—Asn—Asp—Leu—OH
[c]HSV 4-15 = H—Ser—Thr—Ser—Tyr—Ala—Gly—Ala—Val—Val—Asn—Asp—Leu—OH
[d]HSV 1-15* = H—Val—Ser—Arg—Ser—Thr—Ser—Tyr—Ala—Gly—Ala—Val—Val—Asn—Asp—Leu—OH
[e]HSV 1-15 = H—Glu—Cys—Arg—Ser—Thr—Ser—Tyr—Ala—Gly—Ala—Val—Val—Asn—Asp—Leu—OH
[f]EBV 7-15 = H—Tyr—Thr—Met—Leu—Val—Val—Asp—Asp—Leu—OH

EXAMPLE 4

Therapeutic Effect of HSV 7-15 Peptide and Combinations Thereof on Cutaneous Herpes Virus Infection in Guinea Pigs.

Viruses: HSV-1 strain MP-12 having a titer of 4.8×10$^7$ PFU/ml, and HSV-2 strain HG-52 having a titer of 6×10$^7$ PFU/ml were utilized. These strains have been described by A. L. Epstein and B. Jacquemont, J. Gen. Virol., 64, 1499 (1983) and by Y. Langelier and G. Buttin, J. Gen. Virol., 57, 21 (1981), respectively.

Animals: Dunkin-Hartley guinea pigs (550-630 g) obtained from Canadian Breeding Farm, St-Constant, Quebec, Canada were used. Food and drinking water were given ad libitum.

Inoculation Procedure: Seven guinea pigs were anesthetized with sodium pentobarbital (50 mg/kg, ip). Their backs were shaved with an electric razor, depilated with a commercial hair depilator (Neet®), washed and dried. Their toenails were cut and rounded off. The hairless area of their backs was divided into six distinct zones with a marking pencil. Four animals were inoculated with the HSV-1 and three were inoculated with the HSV-2 as follows: an application of 20 μl of the virus was applied to the center of each zone; thereafter, the area of application of each zone was punctured 60 times to a depth of 1 mm with a 26⅝ gauge syringe needle. The animals awoke from their postanesthetic sleep about two hours after being anesthetized and resumed normal activity.

Treatment: The following formulations were used. Note: Prior to use, the emulsions were blended at high speed in an emulsifier (POLYTRON®), cooled in an ice bath for 30 minutes and then stored at 4° C. until use.

1. Control emulsion: a mixture of 11.25 ml of saline (0.85% NaCl in H$_2$O), 13.75 ml of sesame oil (Sigma Chemical Co., St. Louis, Mo., U.S.A.) and 25 mg of bovine serum albumin (Sigma Chemical Co).

2. Peptide emulsion: the same as the control emulsion except that the BSA is replaced with an equal weight of the HSV 7-15 peptide.

3. Acyclovir ointment 5% (ZORIVAX®, Burroughs Wellcome, Inc.).

4. Bacitracin emulsion: the same as the control emulsion except that the BSA is replaced with an equal weight of bacitracin (Sigma Chemical Co.).

5. Peptide-bacitracin emulsion: a mixture of 11.25 ml of saline, 13.75 ml of sesame oil, 25 mg of HSV 7-15 peptide and 25 mg of bacitracin.

Treatment began on the day following the inoculation (noted as Day 1 in Tables III and IV hereinafter). The treatment comprised applying 100 μl of a formulation to five of the six above mentioned zones (a different formulation for each zone). The sixth zone was given a treatment comprising 50 μl each of the peptide - bacitracin emulsion and the acyclovir ointment 5%. Treatments were performed twice daily, once in the morning and once in the evening.

Evaluation of Results: The inoculated areas were scored daily, prior to the morning treatment for the duration of the experiment. The scoring was done blind according to scoring system of S. Alenius and B. Oberg, Archives of Virology, 58, 277 (1978). The scoring system is reproduced in TABLE II. The results are shown in TABLES III and IV. All scoring was confirmed single blind by an independent observer. The score for any given day was obtained by the addition of all score numbers read for each animal in the HSV-1 infected group or the HSV-2 infected group, divided by the number of animals in that group.

TABLE II

| Scoring system for HSV infection on quinea pig skin | |
|---|---|
| Appearance of inoculated skin score | |
| Erythematous and slightly edematous | 0.5 |
| Erythema and one or two small vesicles | 1 |
| Erythema and numerous small vesicles | 2 |
| Numerous large vesicles & if in close juxtaposition, coalesced | 3 |
| Vesicles dried, large crusts | 3 |
| Crusts fallen off to ca. 50 percent | 2 |
| Circa 10 percent of the crusts remaining | 1 |
| Uninfected or healed area, no crusts or vesicles. | 0 |
| Trauma from the inoculation or traces from the infection can be present | |

TABLE III

| | HSV-1 Infected Group of Guinea Pigs | | | | | | | | | | |
|---|---|---|---|---|---|---|---|---|---|---|---|
| | DAY | | | | | | | | | | |
| | 1 | 2 | 3 | 4 | 5 | 6 | 7 | 8 | 9 | 10 | 11 |
| Control Emulsion | 0.50 | 0.50 | 0.55 | 1.00 | 1.45 | 1.53 | 0.60 | 0.50 | 0.40 | 0.10 | 0.00 |
| Peptide Emulsion | 0.50 | 0.50 | 0.43 | 0.43 | 0.50 | 0.55 | 0.30 | 0.13 | 0.00 | 0.00 | 0.00 |
| Acyclovir | 0.50 | 0.50 | 0.28 | 0.20 | 0.20 | 0.20 | 0.15 | 0.00 | 0.00 | 0.00 | 0.00 |
| Bacitracin Emulsion | 0.50 | 0.50 | 0.50 | 0.80 | 0.65 | 0.78 | 0.13 | 0.07 | 0.07 | 0.00 | 0.00 |
| Peptide-Bacitracin Emulsion | 0.50 | 0.50 | 0.20 | 0.28 | 0.28 | 0.28 | 0.00 | 0.00 | 0.00 | 0.00 | 0.00 |
| Peptide-Bacitracin Emulsion + Acyclovir | 0.50 | 0.50 | 0.48 | 0.48 | 0.28 | 0.28 | 0.05 | 0.00 | 0.00 | 0.00 | 0.00 |

TABLE IV

| | HSV-2 Infected Group of Guinea Pigs | | | | | | | | | | |
|---|---|---|---|---|---|---|---|---|---|---|---|
| | DAY | | | | | | | | | | |
| | 1 | 2 | 3 | 4 | 5 | 6 | 7 | 8 | 9 | 10 | 11 |
| Control Emulsion | 0.50 | 0.50 | 0.63 | 1.00 | 2.30 | 2.50 | 1.13 | 0.80 | 0.63 | 0.47 | 0.30 |
| Peptide Emulsion | 0.50 | 0.50 | 0.57 | 0.73 | 1.50 | 1.73 | 0.63 | 0.53 | 0.50 | 0.20 | 0.07 |
| Acyclovir | 0.50 | 0.50 | 0.63 | 0.67 | 1.23 | 0.57 | 0.40 | 0.13 | 0.13 | 0.00 | 0.00 |
| Bacitracin Emulsion | 0.50 | 0.50 | 0.57 | 0.83 | 1.90 | 2.13 | 0.90 | 0.63 | 0.40 | 0.07 | 0.00 |
| Peptide-Bacitracin Emulsion | 0.50 | 0.50 | 0.43 | 0.50 | 1.23 | 1.23 | 0.63 | 0.40 | 0.20 | 0.13 | 0.00 |
| Peptide-Bacitracin Emulsion + Acyclovir | 0.50 | 0.50 | 0.50 | 0.70 | 1.23 | 0.90 | 0.40 | 0.30 | 0.07 | 0.07 | 0.00 |

With respect to shortening the healing time and diminishing the symptoms of HSV-1 infection, TABLE III shows that HSV 7-15 peptide and its combinations with bacitracin and with bacitracin plus acyclovir are effective, and that the combination of the HSV 7-15 peptide and bacitracin is superior in these two parameters to either of the latter two compounds alone. The shortening of the healing time with the combination of the peptide and bacitracin is noteworthy. Likewise, TABLE IV shows that the HSV 7-15 peptide and such combinations are effective against HSV-2 with respect to shortening healing time and alleviating the symptoms of the virus, and that the peptide bacitracin combination significantly reduces the symptoms of the herpes simplex as compared to the peptide and bacitracin alone.

EXAMPLE 5

Comparison of HSV 7-15 Peptide, Bacitracin and the Combination of the Two Agents in Inhibiting HSV-2 Replication Using Cell Culture Techniques a) Preparation of serum-starved cells: A medium composed of alpha medium (Gibco Canada Inc, Burlington, Ontario, Canada) and fetal calf serum (Gibco Canada Inc.), in a 9:1 volume ratio, was placed in tissue culture dishes (35 mm, A/S Nunc, Kamstrup, Denmark). The medium in each dish was seeded with BHK 21/C13 cells ($1.5 \times 10^6$ for each dish). (BHK 21/C13 cells have been described by Langelier and Buttin, supra.) After 6 hours, the medium was replaced with a new medium composed of alpha medium and fetal calf serum (99.5:0.5,v/v). The resultant preparation was incubated at 37° C. for 4 days.

b) Cell infection in BBMT medium*without serum: The incubation medium is removed from the cells. The cells are washed twice with alpha medium (without the serum) and once with the BBMT medium. The cells are then incubated at 37° C. in BBMT medium for 2 hours. The stock of HSV-2, described in Example 4, is diluted with BBMT medium, with or without the agents (conc.=1 mM) to be tested, to obtain new stock preparations having a multiplicity of infection of 0.02 PFU/cell. Thus four stock solutions of the virus were prepared for each virus, one without any of the agents (control), one with HSV 7-15 peptide (1mM), one with bacitracin (1mM) and one containing HSV 7-15 peptide (1mM) and bacitracin (1mM).

* BBMT medium is described by P. Brazeau et al., Proc. Natl. Acad. Sci. USA, 79, 7909(1982).

Each stock solution (250 μl) is added to separate dishes of the previously prepared cells in BBMT medium. After one hour for absorption of the virus, the medium is aspirated from the dishes and the cells washed twice with BBMT medium. BBMT medium (400 μl), with or without the respective 0.1mM concentrations of the agents being assayed, is then added to the dishes containing the cells.

c) Harvesting: At appropriate times, cells are detached with a rubber policeman and frozen at −80° C. until titration.

d) Titration: Virus titration is performed according to the method of B. B. Wentworth and L. French, Proc. Soc. Exp. Biol. Med., 131, 588 (1969).

The results are shown in TABLE V expressed in PFU/cell; B refers to values obtained before absorption and A refers to values obtained after absorption.

TABLE V

| Time (Hours, post infection) | Cell Culture Assay | | | | | | |
|---|---|---|---|---|---|---|---|
| | Control | Peptide (C = 1 mM) | | Bacitracin (C = 1 mM) | | Peptide (c = 1 mM) + Bacitracin (c = 1 mM) | |
| | | B | A | B | A | B | A |
| 4 | 0.0008 | 0.0006 | 0.001 | 0.0007 | 0.0005 | 0.0004 | 0.0004 |
| 12 | 0.04 | 0.006 | 0.01 | 0.005 | 0.007 | 0.0015 | 0.0014 |
| 24 | 16.0 | 0.4 | 0.5 | 0.06 | 0.06 | 0.01 | 0.015 |

TABLE V-continued

| Time (Hours, post infection) | Control | Cell Culture Assay | | | | Peptide (c = 1 mM) + Bacitracin (c = 1 mM) | |
|---|---|---|---|---|---|---|---|
| | | Peptide (C = 1 mM) | | Bacitracin (C = 1 mM) | | | |
| | | B | A | B | A | B | A |
| 36 | 32.0 | 0.8 | 1.1 | 0.03 | 0.06 | 0.0012 | 0.003 |

The results expressed in Table IV show that the combination of bacitracin and the HSV 7-15 peptide is able to decrease the actual viral production titer to a much greater degree (i.e. one twenty seven thousandth after 36 hours) than either of the agents alone.

EXAMPLE 6

Structure and Enzyme Inhibiting Activity of Other Peptides of Formula 1

By following the screening procedure of Example 2, other peptides of formula 1 have been evaluated for their ability to specifically inhibit herpes simplex viral ribonucleotide reductase. The structure and assay results for a number of these peptides are listed in Table VI.

Results for each peptide are expressed as the concentration (micromoles) of the peptide producing 50% of the maximal inhibition $IC_{50}$) of enzyme activity. The specific activity of the enzyme preparartion is 75 μg (21.6 units mg$^{-1}$). The results are based on the activity obtained in control experiments without peptide and represent the mean of four assays that varied less than 10% with each other. Ac, acetyl; β-Ala, L-β-alanyl; desamino-Tyr, 3-(4-hydroxyphenyl)propionyl; Tyr(Me), L-0-methyltyrosyl; 4-NO$_2$-Phe, 4-nitrophenylalanyl; 4-NH$_2$-Phe, 4-amino-L-phenylalanyl; 4-N$_3$-Phe, 4-azido-L-phenylalanyl

TABLE VI

| Formula (R$^7$ R$^8$ R$^9$ R$^{10}$ R$^{11}$ R$^{12}$ R$^{13}$ R$^{14}$ R$^{15}$) | IC$_{50}$ |
|---|---|
| Ac—Tyr—Ala—Gly—Ala—Val—Val—Asn—Asp—Leu—OH | 20 |
| H—Tyr—Ala—Gly—Ala—Val—Val—Asn—Asp—Leu—NH$_2$ | 190 |
| Ac—Tyr—Ala—Gly—Ala—Val—Val—Asn—Asp—Leu—NH$_2$ | 76 |
| H—Tyr—Ala—Val—Val—Asn—Asp—Leu—OH | 340 |
| Ac—Tyr—Ala—Val—Val—Asn—Asp—Leu—OH | 330 |
| Ac—Tyr—Gly—Ala—Val—Val—Asn—Asp—Leu—OH | 150 |
| H—D—Tyr—Ala—Gly—Ala—Val—Val—Asn—Asp—Leu—OH | 200 |
| Ac—D—Tyr—Ala—Gly—Ala—Val—Val—Asn—Asp—Leu—OH | 165 |
| H—Tyr(OMe)—Ala—Gly—Ala—Val—Val—Asn—Asp—Leu—OH | 88 |
| Ac—Tyr(OMe)—Ala—Gly—Ala—Val—Val—Asn—Asp—Leu—OH | 40 |
| (desamino-Tyr)—Ala—Gly—Ala—Val—Val—Asn—Asp—Leu—OH | 33 |
| H—Tyr—D—Ala—Gly—Ala—Val—Val—Asn—Asp—Leu—OH | 200 |
| Ac—Tyr—D—Ala—Gly—Ala—Val—Val—Asn—Asp—Leu—OH | 230 |
| H—Tyr-β-Ala—Gly—Ala—Val—Val—Asn—Asp—Leu—OH | 100 |
| H—Tyr—Ala—Gly—Thr—Val—Ile—Asn—Asp—Leu—OH | 15 |
| Ac—Tyr—Ala—Gly—Thr—Val—Ile—Asn—Asp—Leu—OH | 2 |
| Ac—Phe—Val—Ile—Asn—Asp—Leu—OH | 42 |
| H—Phe—Ala—Gly—Ala—Val—Val—Asn—Asp—Leu—OH | 68 |
| H—His—Ala—Gly—Ala—Val—Val—Asn—Asp—Leu—OH | 400 |
| H—Tyr—Ser—Gly—Ala—Val—Val—Asn—Asp—Leu—OH | 90 |
| Ac—Tyr—Ser—Val—Ile—Asn—Asp—Leu—OH | 77 |
| H—Tyr—Val—Val—Asn—Asp—Leu—OH | 81 |
| desamino-Tyr—Val—Ile—Asn—Asp—Leu—OH | 17 |
| H—Tyr—Ala—Gly—Ala—Val—Leu—Asp—Asp—Leu—OH | 90 |
| Ac—Tyr—Ala—Gly—Thr—Val—Ile—Asn—Asp—Leu—OH | 5.2 |
| Ac—Tyr—Ala—Gly—Thr—Val—Ile—Gln—Asp—Leu—OH | 36.5 |
| H—Tyr—Ala—Gly—Ala—Val—Val—Asn—Asp—Ile—OH | 110 |
| H—(4-NO$_2$-Phe)—Tyr—Ala—Gly—Ala—Val—Val—Asn—Asp—Ile—OH | 6.8 |
| H—(4-NH$_2$-Phe)—Tyr—Ala—Gly—Ala—Val—Val—Asn—Asp—Ile—OH | 15 |
| H—(4-N$_3$-Phe)—Tyr—Ala—Gly—Ala—Val—Val—Asn—Asp—Ile—OH | 28 |
| Ac—Tyr—Val—Val—Asn—Asp—Leu—OH | 31 |
| Ac—Tyr—Val—Ile—Asn—Asp—Leu—OH | 27 |
| Ac—Tyr—Ala—Gly—Thr—Ile—Val—Asn—Asp—Leu—OH | 4.9 |
| Ac—Tyr(OMe)—Val—Ile—Asn—Asp—Leu—OH | 24 |
| Ac—Tyr—Ala—Gly—Phe—Val—Ile—Asn—Asp—Leu—OH | 4.2 |
| Ac—Tyr(OAc)—Ala—Gly—Phe—Val—Ile—Asn—Asp—Leu—OH | 14 |
| H—Tyr—Ala—Pro—Ala—Val—Ile—Asn—Asp—Leu—OH | 37 |
| H—Tyr—Ala—Gly—Pro—Val—Val—Asn—Asp—Leu—OH | 48 |
| H—Lys—Tyr—Ala—Gly—Ala—Val—Val—Asn—Asp—Leu—OH | 68 |
| Ac—Tyr—Ala—Gly—Thr—Ile—Ile—Asn—Asp—Leu—OH | 2.6 |
| Ac—Tyr—Ala—Gly—Ser—Val—Ile—Asn—Asp—Leu—OH | 5.0 |
| Ac—Tyr—Ala—Gly—Val—Val—Ile—Asn—Asp—Leu—OH | 4.3 |
| Ac—Tyr—Ala—Gly—Cys—Val—Ile—Asn—Asp—Leu—OH | 3.9 |
| Ac—Tyr—Ala—Ala—Thr—Val—Ile—Asn—Asp—Leu—OH | 15 |
| Ac—Tyr—Ala—Val—Thr—Val—Ile—Asn—Asp—Leu—OH | 4.6 |
| Ac—Tyr—Ser—Gly—Thr—Val—Ile—Asn—Asp—Leu—OH | 1.9 |
| Ac—Tyr—Cys—Gly—Thr—Val—Ile—Asn—Asp—Leu—OH | 3.1 |
| NH$_2$(CH$_2$)$_7$CO—Tyr—Ala—Gly—Ala—Val—Val—Asn—Asp—Leu—OH | 12.3 |

We claim:

1. A polypeptide selected from a group consisting of the following polypeptide

H—Tyr—Ala—Gly—Thr—Val—Ile—Asn—Asp—Leu—OH, (18-1)

Ac—Tyr—Ala—Gly—Thr—Val—Ile—Asn—Asp—Leu—OH, (18-2)

Ac—Tyr(OAc)—Ala—Gly—Phe—Val—Ile—Asn—Asp—Leu—OH, (18-3)

Ac—Tyr—Ala—Gly—Ser—Val—Ile—Asn—Asp—Leu—OH, (18-4)

Ac—Tyr—Ala—Gly—Val—Val—Ile—Asn—Asp—Leu—OH, (18-5)

Ac—Tyr—Ala—Gly—Cys—Val—Ile—Asn—Asp—Leu—OH, (18-6)

Ac—Tyr—Ala—Ala—Thr—Val—Ile—Asn—Asp—Leu—OH, (18-7)

Ac—Tyr—Ala—Val—Thr—Val—Ile—Asn—Asp—Leu—OH, (18-8)

Ac—Tyr—Ser—Gly—Thr—Val—Ile—Asn—Asp—Leu—OH, (18-9)

Ac—Tyr—Cys—Gly—Thr—Val—Ile—Asn—Asp—Leu—OH, (18-10)

Ac—Tyr—Ala—Gly—Phe—Val—Ile—Asn—Asp—Leu—OH, (18-11)

Ac—Tyr—Ala—Pro—Ala—Val—Ile—Asn—Asp—Leu—OH, (18-12)

Ac—Tyr—Ser—Val—Ile—Asn—Asp—Leu—OH, (18-13)

Ac—Phe—Val—Ile—Asn—Asp—Leu—OH, (18-14)

desamino—Tyr—Val—Ile—Asn—Asp—Leu—OH, (18-15)

Ac—Tyr—Val—Ile—Asn—Asp—Leu—OH, (18-16)

and

Ac—Tyr(OMe)—Val—Ile—Asn—Asp—Leu—OH, (18-17)

or a therapeutically acceptable salt of said polypeptide.

or a therapeutically acceptable salt of said polypetide.

* * * * *